(12) United States Patent
Cheng et al.

(10) Patent No.: US 8,241,904 B2
(45) Date of Patent: *Aug. 14, 2012

(54) SYSTEM AND METHOD FOR CONTROLLING A MAMMALIAN CELL CULTURE PROCESS

(75) Inventors: Alan T. Y. Cheng, Naperville, IL (US); Ying Zhou, Naperville, IL (US); Balazs Hunek, Chicago, IL (US); Amitabh Gupta, Naperville, IL (US); Nigel Grinter, Buffalo Grove, IL (US)

(73) Assignee: Praxair Technology, Inc., Danbury, CT (US)

( * ) Notice: Subject to any disclaimer, the term of this patent is extended or adjusted under 35 U.S.C. 154(b) by 347 days.

This patent is subject to a terminal disclaimer.

(21) Appl. No.: 12/536,559

(22) Filed: Aug. 6, 2009

(65) Prior Publication Data

US 2010/0035343 A1 Feb. 11, 2010

Related U.S. Application Data

(60) Provisional application No. 61/086,665, filed on Aug. 6, 2008, provisional application No. 61/086,685, filed on Aug. 6, 2008.

(51) Int. Cl.
*C12N 5/02* (2006.01)
(52) U.S. Cl. .......... 435/383; 435/289.1; 435/300.1; 435/3; 435/295.2
(58) Field of Classification Search .............. None
See application file for complete search history.

(56) References Cited

U.S. PATENT DOCUMENTS 2,530,814 A 11/1950 Becze et al.
2009/0280565 A1 11/2009 Jolicoeur et al.

OTHER PUBLICATIONS

Jolicoeur, M. et al., "Development of a Helical-Ribbon Impeller Bioreactor for High-Density Plant Cell Suspension Culture", *Biotechnology and Bioengineering*, vol. 39, pp. 511-521 (1992). XP-002548862.
Dezengotita, V.M., et al., "Effects of $CO_2$ and osmolality on hybridoma cells: growth, metabolism and monoclonal antibody production", *Cytotechnology*, vol. 28, No. 1-3, pp. 213-227 (1998). XP-019236586.
De Dobbeleer, C., et al., "A High-Rate Perfusion Bioreactor for Plant Cells", *Biotechnology and Bioengineering*, vol. 95, No. 6, pp. 1126-1137 (2006). XP-003015870.
Kimura, R., et al., "Effects of Elevated $pCO_2$ and/or Osmolality on the Growth and Recombinant tPA Production of CHO Cells", *Biotechnology and Bioengineering*, vol. 52, No. 1, pp. 152-160 (1996). XP-002536930.
Nienow, A.W., "Reactor engineering in large scale animal cell culture", *Cytotechnology*, vol. 50, No. 1-3, pp. 9-33 (2006). XP-019393910.
Zhu, M.M., et al., "Effects of Elevated $pCO_2$ and Osmolality on Growth of CHO Cells and Production of Antibody-Fusion Protein B1: A Case Study", *Biotechnology Progress*, vol. 21, No. 1, pp. 70-77 (2005). XP-002536931.

*Primary Examiner* — Jim Ketter
(74) *Attorney, Agent, or Firm* — Robert J. Hampsch

(57) ABSTRACT

A system and method for controlling a mammalian cell culture process are provided. Such control of the cell culture process involves control of the level of dissolved carbon dioxide in the cell culture media and the resulting ability to prevent increases in the osmolality level is achieved by enhanced stripping of carbon dioxide with little or no damage to the mammalian cells. The disclosed methods and systems of dissolved carbon dioxide stripping include enhanced surface gas exchange mechanisms within the bioreactor vessel through the use of an upward flow impeller combined with vertical baffles to convert swirling motions of the liquid into a largely vertical flow.

24 Claims, 5 Drawing Sheets

SYSTEM AND METHOD FOR CONTROLLING A MAMMALIAN CELL CULTURE PROCESS

CROSS REFERENCE TO RELATED APPLICATIONS

The present application claims priority from U.S. provisional patent application Ser. Nos. 61/086,665 and 61/086,685 both filed Aug. 6, 2008, the disclosures of which are incorporated by reference herein.

FIELD OF THE INVENTION

The present invention relates to cell culture processes, and more particularly to methods and systems of controlling the level of dissolved carbon dioxide in a mammalian cell culture process, and still more particularly to methods and systems of stripping or removing carbon dioxide during a mammalian cell culture process and enhancing other process conditions such as reduction of shear-related damage to cells and prevention of osmolality increases to inhibitory levels.

BACKGROUND

Commercial production of protein therapeutics and other biological products such as monoclonal antibodies is presently carried out generally in bioreactors adapted for culturing suspensions of genetically optimized mammalian, insect or other cell types. Mammalian cell culture bioreactors typically have several hundred to several thousand liters in working volume. Most common full scale manufacturing plants have bioreactors with working volumes ranging from approximately 1,000 liters up to 25,000 liters. Drug candidates for clinical trials are produced in laboratory scale bioreactors having five (5) liters to several hundred liters of working volume.

The optimization to achieve the highest biological product yields possible in the smallest amount of time and the related challenges of bioreactor scale-up have focused on the control of recognized critical process parameters such as pH, dissolved oxygen (DO), temperature, nutrient composition and by-product profiles, agitation profile, gas sparging method, nutrient feed and product harvest profiles. The importance of other process parameters such as dissolved carbon dioxide ($dCO_2$) and osmolality (i.e. concentration of dissolved particles per kilogram of solution) is just recently being documented in the literature. As a matter of fact, many commercial bioreactors do not even have the means installed to measure dissolved carbon dioxide and/or osmolality levels in-situ, let alone a means to control and optimize those parameters. Depending on the scale of the commercial operation—ranging from hundreds up to 25,000 liters of bioreactor volume—scale-up, optimization and control of the process pose different challenges. At commercial scales above about 1,000 liters, simultaneous and independent control of dissolved carbon dioxide and osmolality levels becomes difficult if not impossible with current best available technologies and methodologies.

Before a manufacturing-scale mammalian cell cultivation process starts in a bioreactor, a seed culture inoculum is typically prepared. This involves culturing production cells in a series of flasks in incubators and/or smaller bioreactors of increasing volume until enough cells are available for inoculation into the production bioreactor. The process involves transferring a cell population from one culture vessel to a larger one. Generally, a 20% dilution of the cell population is used for each transfer or subculture. In the incubator, the flasks with culture medium are clamped to a rotating platform to swirl the culture and facilitate gas transfer between the culture medium and the atmosphere in the incubators. Typically, the incubator for a mammalian cell culture process is set at 37° C. with 5% carbon dioxide ($CO_2$) and a humidity level higher than about 80%. Similar temperatures and $CO_2$ levels are used for seed cultures grown in bioreactors. When the seed culture reaches a sufficient volume and cell density, it is inoculated into the production bioreactor.

After seed culture is inoculated into the bioreactor medium, parameters such as pH, temperature, and level of dissolved oxygen are controlled to the prescribed levels during the cell cultivation process. pH is typically controlled by adding basic or acidic solutions when necessary during the process. Commonly used base solutions include sodium bicarbonate, sodium carbonate and sodium hydroxide solutions. Dissolution of carbon dioxide ($CO_2$) is commonly used to achieve a more acidic pH. The preferred temperature of the culture medium or solution for mammalian cell cultivation processes is about 37° C. The desired level of dissolved oxygen in the culture medium or solution is typically achieved through air sparging using sparger installed on the bottom of the bioreactor, along with agitation of the culture medium or solution using impellers which breakup the large air/oxygen bubbles to enhance the transfer of oxygen to the cell medium from the sparged air bubbles. Purging the bioreactor headspace with a cover gas provides a limited degree of surface gas exchange. Disadvantageously, air-sparging and agitation of the culture medium or solution may result in foaming and shear damage to the mammalian cells which adversely impacts cell viability. Accumulations of foam on the surface of the culture medium also serve to further limit surface gas exchange and to reduce the available working volume of the bioreactor.

Commercial-scale mammalian cell cultivation processes may be conducted in three different operation modes: batch mode or fed-batch mode for suspended cell cultures, and perfusion mode for immobilized cells. The majority of the commercial-scale mammalian cell cultivation processes are operated in fed-batch mode. In fed-batch mode, additional media and nutrients are added to the bioreactor at different times during the cell cultivation process to supplement the carbon source and other nutrients after initial bioreactor setup.

Before any bioreactor is used for mammalian cell cultivation, it typically must be sterilized and equipped with various probes as well as connections for supplemental gas supply and introduction of additional feeds. Temperature probes, pH detectors, dissolved oxygen probes and dissolved $CO_2$ probes or sensors are used to monitor the temperature, pH, dissolved oxygen and dissolved $CO_2$ levels of the cell medium or solution in real time. In addition, cell culture medium or solution samples can be withdrawn from the bioreactor at selected intervals to determine cell density and cell viability, as well as to analyze other characteristics such as metabolites and osmolality. Based on such analytical results, additional feed or other additives can be added to the cell culture medium or solution in an effort to prolong the cell viability and increase production of biological products. When cell viability reaches a prescribed lower threshold, the cell cultivation process can be stopped or shut down. The prescribed lower threshold is often determined empirically based on the results of down-stream recovery and purification of the harvested biological products.

During the cultivation process, the mammalian cells exhibit three phases, namely the lag phase, the exponential growth phase, and the stationary or production phase. The lag phase occurs immediately after inoculation and is generally a period of physiological adaptation of mammalian cells to the new environment. After the lag phase, the mammalian cells are considered in the exponential growth phase. In the exponential growth phase, the mammalian cells multiply and cell density increases exponentially with time. Many cells actually start to produce the desired protein, antibody or biological product during some point in the exponential growth phase. Cell density refers to the total number of cells in culture, usually indicated in the density of viable and non-viable cells. When the mammalian cells reach the stationary or production phase, the viable cells are actively producing the biological products for downstream harvesting. During this phase, the total cell density may remain generally constant, but the cell viability (i.e. the percentage of viable cells) tends to decrease rapidly over time.

Mammalian cells are known to be sensitive to the amount of dissolved carbon dioxide in the cell culture media or solution. Mammalian cell cultures exposed to excess carbon dioxide levels during the exponential growth phase may demonstrate reduced production of monoclonal antibodies or other desired biological products. Before inoculation, the pH of the slightly alkaline culture media is often reduced to a more optimal value by addition of carbon dioxide. This process often leads to elevated levels of dissolved carbon dioxide at the beginning of the lag phase of many mammalian cell culture processes.

Dissolved carbon dioxide in mammalian cell culture bioreactors originates from chemical and biological sources. The chemical source of carbon dioxide is equilibrium chemical reactions occurring within the cell culture medium or solution that includes a selected amount of a buffer solution containing sodium bicarbonate and/or sodium carbonate. Additionally, carbon dioxide may be directly sparged into the slightly alkaline culture medium or solution to reduce the pH level of the broth to a prescribed level, usually around 7.0, resulting in more dissolved carbon dioxide. The biological source of carbon dioxide is a product of the respiration of the mammalian cells within the bioreactor. This biological source of carbon dioxide increases with cell density and generally reaches its maximum value at about the same time that cell density within the bioreactor is maximized. However, as more carbon dioxide is produced, the pH of the cell culture medium trends toward acidic such that additional bicarbonate is needed to keep the pH of the cell culture medium or solution within the desired range.

To offset the effects of increased dissolved carbon dioxide, one may add sodium bicarbonate so as to maintain the pH of the solution within the prescribed range or attempt to strip the carbon dioxide from the solution by sparging with additional air. Both of these means to offset the effects of increased carbon dioxide have other negative consequences on the mammalian cell culture process.

First, adding sodium bicarbonate to adjust the pH of the solution, results in an increase in osmolality level. Osmolality level represents the number of dissolved particles per kilogram of solution and is commonly reported as mOsm/kg by freeze-point depression. It is known in the art that increased levels of either dissolved carbon dioxide or increased levels of osmolality have adverse or negative impacts on cell density or yield. However, the combined or synergistic effects of carbon dioxide and osmolality levels are not well understood.

Carbon dioxide dissociates into bicarbonate ions at a pH of 7 in water. Only a fraction of the carbon dioxide remains as free $CO_2$ in an un-dissociated state. Removing the dissolved carbon dioxide from a cell culture thus becomes difficult as most mammalian cell cultures take place at pH levels in the range of 6.5 to 7.5. The dissociated bicarbonate ions are not easily removed and generally must be recombined into free carbon dioxide before they can be stripped out of the solution. Any addition of sodium bicarbonate to balance the pH will also increase the equilibrium dissolved carbon dioxide concentration or saturation level in the solution, making it more difficult to remove the carbon dioxide physically.

Conventional methods of removing or stripping dissolved carbon dioxide from a mammalian cell culture solution is by sparging the cell culture solution with air or a gas mixture of air/oxygen/nitrogen in agitated tanks. However, gas sparging in agitated tanks results in adverse effects to the cell culture process. In particular, the gas-bubble breakage at the tip of the rotating agitator is a source of high shear rate that damages mammalian cell membranes, often sufficiently to cause cell death. Even when damage is sub-lethal, cell productivity is compromised in the period that the damaged membrane is repaired. In most current bioreactors, the agitator is a radial flow type that rotates around the center axis of the reactor vessel, and where the sparged gas and liquid within the reactor vessel are pushed outwards from the center of the reactor vessel to the side wall of the vessel. The main purpose of radial pumping impellers is to break and disperse gas bubbles provided by spargers. Bubble breakage behind the rotating impeller will have a major role in cell death. Small shading vortices formed behind the impeller will also damage cells to a lesser extent. Such impellers impart very little vertical or axial mixing. If multiple radial impellers are used, they may form distinct mixing zones within the reactor vessel. Current commercial axial flow impeller designs are all downward pumping. Downward pumping axial impellers generate vortices that entrain gas from the headspace into the body of the agitated liquid, resulting in gas bubble formation. As mentioned above, gas bubbles have a negative impact on cell growth in that the force of a breaking gas bubble is sufficient to damage the outer membrane of a mammalian cell, and can cause it to burst. Therefore, conventional radial impellers and downward pumping axial impellers are not generally suitable for promoting gas exchange between the liquid surface and the bioreactor headspace as a way to remove carbon dioxide from the cell culture medium.

In commercial scale bioreactors (e.g. 1,000 liters to 25,000 liters), carbon dioxide removal is more difficult than in smaller reactors, and the excess carbon dioxide that tends to accumulate is detrimental to cell growth. During scale-up from a bench or laboratory scale bioreactor to a production or commercial scale bioreactor, a productivity loss of up to 60% has been observed; excessive levels of carbon dioxide at the larger scale is the suspected cause of such productivity loss. Carbon dioxide removal via air sparging tends to be very effective in laboratory or bench scale bioreactors (e.g. less than 10 Liters of working volume) but is less effective in larger scale commercial bioreactors for at least three reasons: (i) the surface area to volume ratio is reduced, which further limits surface gas exchange; (ii) higher hydrostatic pressures in a large vessel increase carbon dioxide solubility; and (iii) larger vessels contain more cells and the resulting increased need for sparged gas to supply oxygen leads to more bubbles, which create more foam at the surface and further inhibit surface gas exchange.

Another disadvantage of foam created by air sparging into a rotating agitator is that cells become trapped on the foam layer where they are depleted of nutrients. Foaming also limits the operable volume of the reactor, as foam overflow can damage the integrities of the biological filters that prevent process contamination. Although anti-foaming agents are used, such agents have many undesirable effects. For example, anti-foaming agents can contaminate the biological products and their removal may require further downstream purification steps. Also, many such anti-foaming agents reduce the interfacial gas-liquid mass transfer efficiencies occurring within the bioreactor.

Also, gas bubbles created by sparging can burst at the liquid surface; this is often more damaging to cultured cells than shear due to the agitator. Minimizing agitator speed and limiting the gas sparging rate are currently viewed as the best means to avoid such damage and increase cell viability. However, both measures reduce the amount of carbon dioxide that is removed which in turn inhibits cell growth and reduces viability. These disadvantages are particularly challenging to overcome in large, commercial-scale bioreactors where the shear rate goes up substantially with the diameter of the impellers.

Some bubble free systems with membrane aeration have been proposed, but these have demonstrated only limited success even at small scales. Membrane fouling, system cost and system scalability have prevented membrane-based bioreactors from gaining broader acceptance.

Wave Bioreactor™ is an example of a design in which the surface to volume ration is large enough for dissolved carbon dioxide to be removed through gas exchange at the surface. Agitation is provided by rocking motion of a mechanically supported tray (See FIG. 1). The surface area needed for sufficient gas exchange has limited the size of this bioreactor to less than 500 liter working volume which is not suitable for large, commercial scale systems.

Conical bioreactors have also been proposed as an alternative way to provide a surface area to volume ratio large enough for gas exchange. The conical bioreactor is supported on an orbital shaker that provides gentle rocking motions. Much like the Wave Bioreactor™, mechanical engineering issues limit this design to smaller bioreactors

SUMMARY OF THE INVENTION

The present invention may be characterized as a bioreactor system for a cell culture process comprising: (a) a bioreactor vessel containing a cell culture medium and defining a headspace; (b) an upward flowing impeller disposed in the bioreactor vessel directing the culture medium in the bioreactor vessel in an upward direction toward the headspace; (c) a gas intake coupled to the to the bioreactor vessel proximate the headspace to deliver a flow of sweep gas from one or more external sources of gas to the headspace of the bioreactor vessel; and (d) a gas exhaust coupled to the bioreactor vessel proximate the headspace to remove the flow of the sweep gas and stripped carbon dioxide from the headspace of the bioreactor vessel to a vent and wherein the upward flowing impeller continuously directs the culture medium in the bioreactor vessel in an upward direction toward the headspace to renew the cell culture medium at the top liquid surface and strip dissolved carbon dioxide from the cell culture medium into the headspace with minimum damage to cells within the cell culture medium.

The present invention may also be characterized as an improvement to a method of culturing cells in a bioreactor vessel, the improvement comprising the steps of: (i) recirculating the cell culture medium within the bioreactor vessel in an upward direction toward a headspace in the bioreactor vessel to renew the cell culture medium at a top liquid surface and r strip dissolved carbon dioxide from the cell culture medium into the headspace with minimum damage to cells within the cell culture medium; and (ii) directing a sweep gas through the headspace of the bioreactor vessel to remove the stripped carbon dioxide from the headspace of the bioreactor vessel to a vent.

BRIEF DESCRIPTION OF THE DRAWINGS

The above and other aspects, features, and advantages of the present invention will be more apparent from the following, more detailed description thereof, presented in conjunction with the following drawings, wherein.

DETAILED DESCRIPTION

Figure 1:
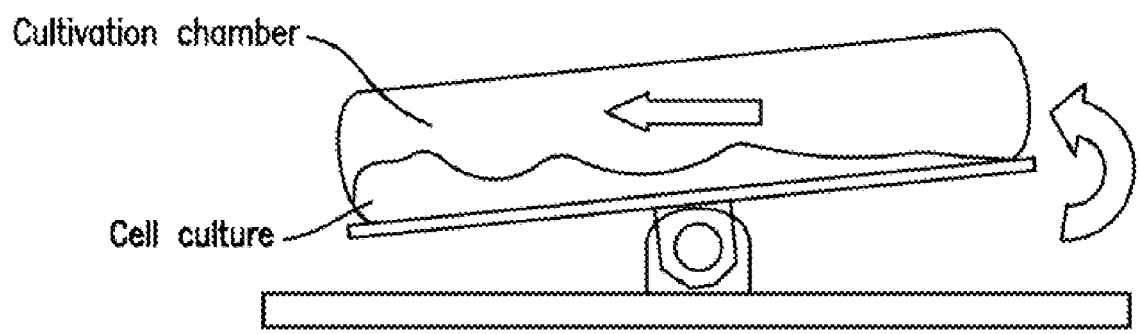
FIG. 1 is a schematic illustration of the prior art Wave Bioreactor™ system.

The majority of the commercial-scale mammalian cell culture manufacturing is done in fed-batch processes where maintaining a relatively constant osmolality, pH and dissolved carbon dioxide level is very challenging. Some academic and private research organizations have expressed concerns over the uncontrolled dissolved $CO_2$ level or osmolality on mammalian cell viability and yield. Contradictory reports can be found for the perceived optimum levels of dissolved $CO_2$ or osmolality. Results are difficult to verify as most academic research was done at very small scales in 6-well dishes without the benefits of pH control or dissolved $CO_2$ measurement. For most industrial scale bioreactors, dissolved $CO_2$ level and osmolality typically are not actively monitored or controlled to provide accurate data. Even if optimum levels of dissolved $CO_2$ or osmolality are predicted, there are no practical methods for removing sufficient dissolved $CO_2$ or of preventing osmolality from rising to non-optimal levels as a result of $CO_2$ accumulation and the consequent pH adjustments.

During the mammalian cell culture fed-batch process, the continuing addition of nutrients and cell boosters tends to increase the cell culture solution osmolality level, while the pH and dissolved carbon dioxide levels in the solution are constantly changing throughout the fed-batch process cycle. Carbon dioxide generated by the mammalian cells during the exponential growth phase often outpaces the carbon dioxide stripping capacity of most current bioreactors, resulting in a continuing increase of the dissolved carbon dioxide levels during the exponential growth phase. As discussed above, this rise in dissolved carbon dioxide levels tends to lower the solution pH and often requires the addition of base to compensate, since controlling the pH of the cell culture medium is viewed as one of the most critical parameters to manage in any mammalian cell culture process. The addition of a base such as bicarbonate further increases the osmolality of the cell culture medium or solution. Base addition also increases the equilibrium level of non-ionized carbon dioxide in solution, making more difficult its removal by gas sparging.

In short, the dissolved carbon dioxide level, pH and osmolality of the cell culture medium or solution are closely interrelated, and the active control of pH and dissolved carbon dioxide level by traditional methods tend to increase osmolality in the cell culture solution to a point where it can negatively impact the process outcome.

Exchange between gas in the headspace and that dissolved in the liquid/solution can occur at the surface of the cell culture solution. Carbon dioxide removal by this means is attractive as compared to stripping via sparged gas since it minimizes shear and bubble damage to cells and reduces or eliminates foaming. Surface gas exchange in commercial scale bioreactors is not presently exploited for carbon dioxide removal, however, since under current process conditions it is far too limited to have practical use. This is a direct consequence of the limited surface to volume ratio of typical conventional bioreactor vessels and the slow rates of culture surface renewal achieved by current agitator designs. These problems become worse in bioreactors with tall and narrow configurations.

Another disadvantage of surface gas exchange in commercial scale bioreactors occurs with the use of rotating shaft agitators. These cause the surface liquid to swirl around in a circle with little tendency for solution from deeper within the vessel to replace it. This has at least two consequences affecting surface gas exchange: first, the surface liquid layer rapidly becomes depleted of dissolved carbon dioxide, lowering the driving force for subsequent $CO_2$ removal to the headspace; second, liquid from the bottom of the bioreactor (where the concentration of dissolved $CO_2$ is greatest thanks to the higher hydrostatic pressures in this region) is only rarely driven to the surface where it can donate dissolved gas to the headspace. The overall effect is that removal of dissolved $CO_2$ is slow and that there is a gradient of dissolved $CO_2$ concentration in the bioreactor, from very low at the surface to high at the bottom where it can easily reach levels that reduce cell productivity and viability.

Figure 2A:
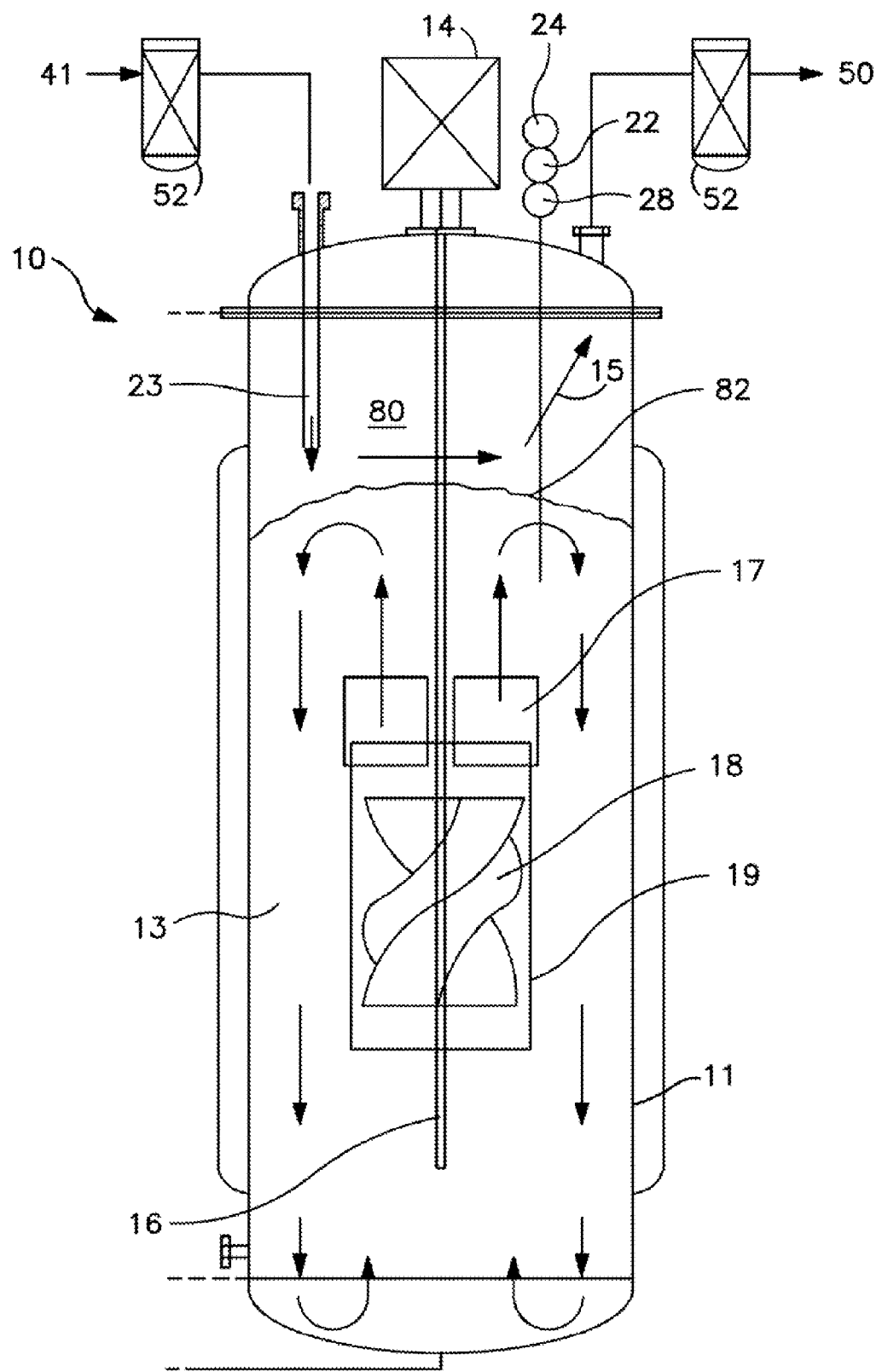
FIG. 2A is a schematic illustration of a bioreactor system employing the upward pumping impeller disposed within a draft tube and having vertical baffles in accordance with an embodiment of the invention.

Turning now to FIG. 2A, there is shown a bioreactor system 10 employing the upward flow impeller 18 disposed within a draft tube 19. The upward pumping impeller 18 is driven via shaft 16 by a motor 14 outside the bioreactor vessel 11 The upward flow of the impeller 18 provides a top surface 82 renewal method that enhances surface gas exchange in a highly controllable manner. The upward pumping impeller 18 moves cell culture medium and suspended mammalian cells from the bottom of the bioreactor vessel 11 toward the liquid/gas interface near the headspace 80 or upper part of the bioreactor vessel 11. In doing so, dissolved carbon dioxide in the cell culture solution or medium is continuously and rapidly brought to the surface of the liquid in the bioreactor vessel 11 where gas-liquid exchange is occurring. A high turnover in the surface liquid allows rapid removal of dissolved carbon dioxide to the headspace 80. The upward flow impeller 18 allows a higher pumping velocity without creating sufficient shear to damage or kill the mammalian cells. The illustrated embodiment also depicts a sweeping gas 15 consisting of oxygen, nitrogen, air, carbon dioxide or other suitable gases and mixtures thereof that is introduced to the headspace 80 in the bioreactor vessel 11 via a dip tube 23, where it interacts with the top surface 82 of the solution to achieve the desired liquid gas exchange, and is subsequently exhausted from the headspace 80 in the bioreactor vessel 11.

Although not shown in FIG. 2A, the bioreactor system 10 includes a plurality of sensors and analyzers including a pH sensor 22, a $dCO_2$ sensor 24, a temperature indicator 26, a dissolved oxygen analyzer 28, and a vent gas analyzer 30. Such sensors and analyzers are coupled as inputs to a system controller (not shown) that controls or adjusts the gas supply 41 of oxygen, nitrogen, and carbon dioxide to the bioreactor vessel 11. The illustrated system 10 also includes an exhaust subsystem 50, a plurality of biological filters 52 and may further include a means for sterilizing the bioreactor vessel with water and steam, as needed. A typical bioreactor control scheme useful in the presently illustrated embodiment as well as a suitable gas supply subsystem, sterilization control system, and exhaust subsystem are shown in more detail in FIGS. 3 and 4.

Referring back to FIG. 2A, the upward pumping impeller 18 is preferably located near the middle of the main bioreactor vessel 11 so that the impeller 18 is submerged for low liquid medium or solution starting levels. The impeller speed is adjustable and may be varied throughout the cell culture process to maintain the desired level of dissolved carbon dioxide at all times for the particular mammalian cell culture process. Preferably, the impeller speed is maintained at very low speeds when the liquid or solution level within the bioreactor vessel is low and should be increased as the liquid or solution level rises. Preferably, a draft tube 19 is to be added to increase the upward flowing velocity, resulting in a higher gas exchange rate. The impeller speed is preferably highest during the end of the exponential growth phase of the cell culture process, when the liquid or solution level in the bioreactor vessel is also highest. Normally, surface gas exchange is an inefficient process as the available surface area is very limited. Any gas exchange occurring between the headspace 80 and the liquid surface 82 will quickly result in gas concentrations on either side of the gas/liquid interface quickly approaching saturation levels. Without proper concentration driving force at the interface, surface aeration is impractical unless measures are implemented to greatly increase the surface area available for gas exchange. Unfortunately, such measures (e.g., atomization of some of the liquid) create excessive shear that would damage and kill fragile mammalian cells. The present system overcomes those limitations, however, by rapidly sweeping the headspace gases to avoid carbon dioxide build up in the gas phase boundary layer. The limitation of the liquid phase boundary layer is also eliminated by the upward pumping action of the submerged impeller.

Figure 2B:
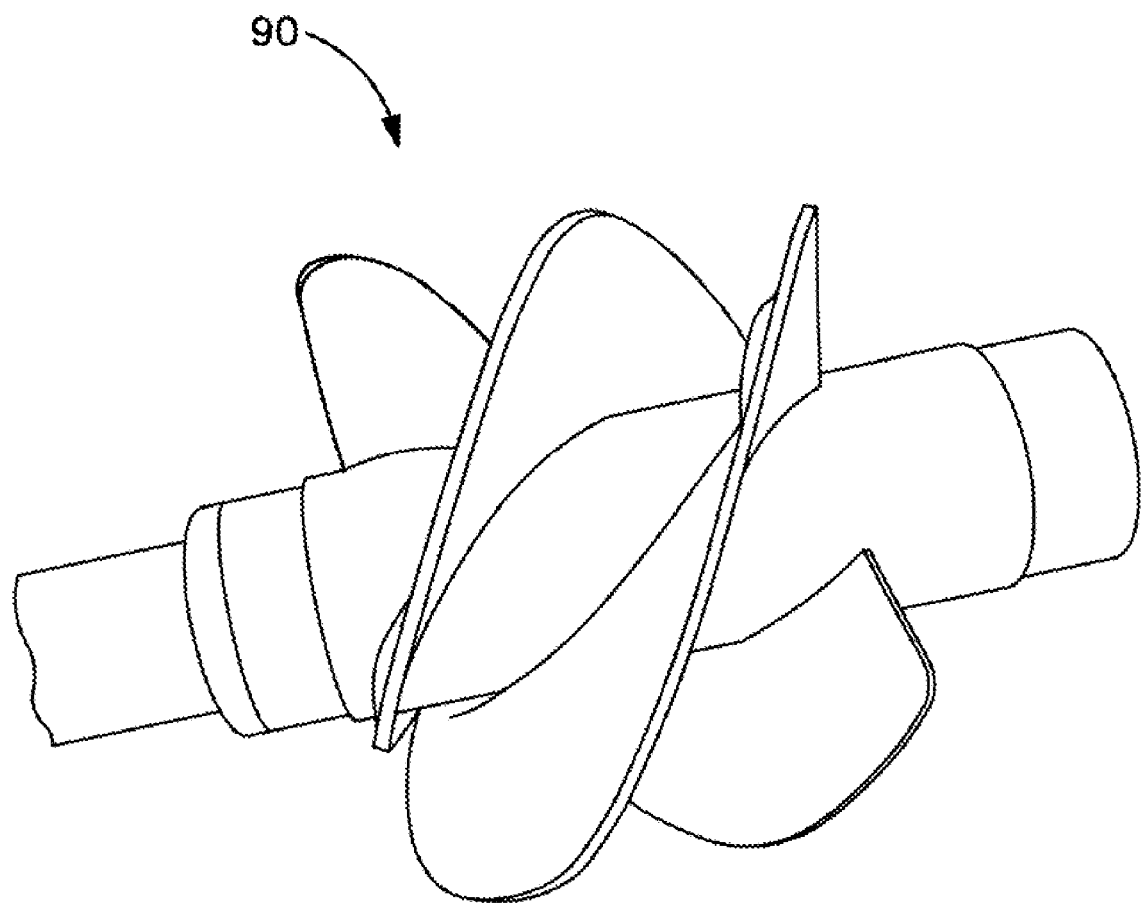
FIG. 2B is an illustration of the upward pumping helical impeller used in an embodiment of the present invention.

It was observed that a number of vertical baffles 17 added on top of the impeller 18 make very large improvements to the gas exchange rate. These vertical baffles 17 translate the rotational velocity into virtually pure vertically oriented flows. To compare the effect of the draft tube 19 and vertical baffles 17 on the dissolved $CO_2$ removal rate through the liquid surface, a carbon dioxide removal test was conducted in a 300 L vessel using the method described in this invention. The solution in the vessel was maintained at a pH of 7 and headspace swept with air. The helical impeller 90 of the type shown in FIG. 2B, was set to run at two different speeds with a frequency inverter. Dissolved $CO_2$ level was measured continuously during the experiment. The results were reported in terms of volumetric mass transfer coefficient ($K_La$) in Table (1).

TABLE 1

| Frequency inverter (Hz) | Without Draft Tube or Baffles $K_La$ (1/hr) | Draft Tube + Baffles $K_La$ (1/hr) | Improvement in Mass Transfer Coefficient % |
| --- | --- | --- | --- |
| 40 | 0.85 | 6.61 | 678% |
| 30 | 1.29 | 4.2 | 226% |

Depending on the speed of the helical impeller, the results showed that the mass transfer coefficient improved between 226% and 678% when a draft tube with baffle was used. Further tests were conducted to show the importance of the vertical baffles on the surface gas exchange phenomena. In these experiments, the helical impeller was installed in the bottom of the 300 L vessel with the vertical baffles removed. From the experimental work of this invention, it was concluded that it is critical to eliminate the swirling movement of the surface liquid (see Table 2). By eliminating swirling motion at the surface, the upward flowing liquid from the impeller emerges quickly from the impeller shaft and spreads across the entire vessel surface, re-submerging into the body of the liquid near the edge of the vessel. With the vertical baffles installed, the carbon dioxide removal rate was improved by 28% to 128%, depending on the rotational speed of the helical impeller. These experimental results show that liquid from the lower part of the bioreactor rapidly replaces the surface liquid, resulting in substantially higher rates of dissolved carbon dioxide removal and oxygen dissolution. Without the vertical baffle, the swirling surface liquid is not significantly replaced by fresh liquid from deeper within the bioreactor.

TABLE 2

| Frequency inverter (Hz) | Draft Tube, w/o Baffles $K_L a$ (1/hr) | Draft Tube with Baffles $K_L a$ (1/hr) | Improvement in Mass Transfer Coefficient % |
| --- | --- | --- | --- |
| 40 | 1.37 | 3.12 | 128% |
| 30 | 1.24 | 1.98 | 60% |
| 20 | 0.8 | 1.02 | 28% |

As discussed above, the liquid or solution in the bottom of a large bioreactor vessel is exposed to significant hydrostatic pressures, and the dissolved carbon dioxide trapped inside the mammalian cells will be slow to equilibrate. The presently disclosed upward pumping impeller mitigates this problem. By recirculating liquid solution and mammalian cells from the bottom of the bioreactor vessel upward to the top surface, the mammalian cells are exposed to a lower overall average hydrostatic pressure regime and thus achieve a better equilibrium level of dissolved carbon dioxide. The continuous axial or upward recirculating of the cell culture medium or solution provides a varying level hydrostatic pressure on the mammalian cells which is believed to enhance the ability of the cells to expel excess dissolved carbon dioxide deep inside the plasma of the cells.

Since there are no deflecting walls or dividers in the bioreactor the upward flowing liquid can reach the top surface very rapidly before rolling outward towards the bioreactor wall. This provides a very rapid renewal of the liquid surface which promotes rapid removal of dissolved carbon dioxide. Alternate forms of impellers can be used to provide the upward recirculating flow with or without the draft tube. Preferably, the upward pumping impeller is a screw impeller or propeller. However, other propellers may also be used so long as the lateral or radial flow from the propeller is minimized which, in turn reduces shearing and other damage to the mammalian cells.

Rapid gas-liquid surface renewal is also useful for dissolving gases into the liquid. For example, the presently disclosed gas-liquid surface renewal method can be used to dissolve the prescribed amount of oxygen needed for the growing cells. When the demand for oxygen is high, the oxygen composition in the sweeping gas in the headspace is increased, resulting in increased transfer of oxygen to the top surface of the recirculating liquid. When the oxygen dissolution requirement is low, the oxygen composition in the sweeping gas in the headspace is reduced and replaced with air or nitrogen. The variation in oxygen composition of the sweeping gas has little or no impact on the carbon dioxide removal rate. The dissolved oxygen concentration is preferably maintained at about 50% in many mammalian cell culture processes. In some cases, such as recombinant protein production from virus infected sf-9 insect cell culture, very low oxygen concentrations (e.g. less than 5% oxygen concentration) are used in the cell culture solution to enhance protein production by the cells.

The dissolved carbon dioxide level can be adjusted or maintained at any desirable level. To decrease the dissolved carbon dioxide level at any time during the cell culture process, the flow rate of the sweeping gas going into the headspace of the bioreactor can be increased to more rapidly eliminate $CO_2$ from the liquid near the surface. The impeller rotational speed can also be increased to speed up the surface liquid renewal rate. To increase the dissolved carbon dioxide level, one would reduce the sweeping gas flow rate and/or decrease rotational speed of the upward pumping impeller. If additional carbon dioxide is needed as, for example, may be the case in the earliest stages of the process shortly after inoculation of the production bioreactor, it can be added to the sweeping gas mixture in the headspace as required. In typical mammalian cell culture processes, the dissolved oxygen requirement increases as the batch proceeds from the initial lag phase to the end of the exponential growth phase, while the dissolved carbon dioxide concentration increases due to cell respiration, reaches a maximum concentration towards the end of the exponential growth phase, and then is gradually reduced during the production phase. Therefore, gaseous carbon dioxide is added mostly during the lag phase to regulate and maintain pH. Also, some prescribed level of dissolved oxygen needs to be maintained during the cell production phase.

In addition to independently adjusting or controlling the nitrogen, oxygen and carbon dioxide concentrations in the sweeping gas mixture, increasing the total headspace gas flow will also avoid accumulation of the stripped gases in the headspace.

In the preferred embodiment, the gas supply of nitrogen, oxygen and carbon dioxide to the bioreactor vessel is introduced above the top surface of the liquid in the headspace and preferably closely adjacent to the rolling surface of the liquid solution in the bioreactor vessel. Such gas introduction can be achieved by making the gas injectors movable so as to always inject the gases at or near the top surface as the liquid level in the bioreactor vessel rises. Impingement of the gas at the rolling top surface reduces the momentum boundary layer on the gas side and improves the total mass transfer rate between the liquid and gas. Alternatively, the gas supply may be delivered using fixed gas injectors disposed so as to introduce the gas at a location near the maximum liquid height that will be attained in the bioreactor vessel. In most mammalian cell culture processes, the maximum liquid height in the bioreactor vessel occurs during the peak of the exponential growth phase where removal of dissolved carbon dioxide is most necessary.

Although not preferred, controlled introduction of the gas supply of nitrogen, air, oxygen and carbon dioxide to the bioreactor vessel may be done by sparging the gases within the solution using one or more spargers disposed within the bioreactor vessel. The sparger used to dissolve oxygen can have finer nozzles (or holes) to generate small oxygen bubbles that dissolve or are absorbed before breaking the liquid surface. The sparger for the stripping gas, typically introduced at considerably higher flow rates, can have much larger nozzles to provide large diameter gas bubbles. Large gas bubbles are less damaging when they break at the surface of the liquid and have less tendency to produce foam. Such submerged gas spargers can assist with the independent control of both oxygen and dissolved carbon dioxide levels in combination with the headspace gas exchange method. When used, the gas spargers are preferably located apart from the upward flow impeller to maximize their residence time in the cell culture medium. With this method, the stripping gas bubbles are much bigger than those injected into axial flow impellers and the potential for foaming is greatly diminished. Gas exchange now occurs both on the surface and in the bulk of the liquid. Sparging small volumes of gases intermittently for short periods of time allows oxygen uptake and carbon dioxide removal to be maximized without resorting to very high flows of sweeping gas or employing the fastest impeller speeds. It is important that such sparging be done only at peak demand for oxygen dissolution and carbon dioxide removal in order to minimize cell damage.

The preferred upward pumping device is a helical impeller that can move large volumes of liquid upward with minimal radial flow. Using a helical impeller, carbon dioxide removal rate was measured from a simulated broth and reported as Volumetric Mass Coefficient. The higher the mass transfer coefficient, the better the gas exchange efficiency. Even with an upward pumping impeller, the moving liquid stream is going to be rotated by the rotation of the agitator. As a result, the surface liquid is going to swirl, greatly reducing liquid surface renewal as the surface liquid rotates in the plane of the surface. To stop the swirling, a vertical baffle system is also used on top of the impeller to break the rotation of the liquid and redirect the flow straight to the surface. Hence, the surface liquid radiates outwards from the shaft at the center of the vessel, spreading and thinning towards the edge of the vessel where it submerges. As a result, the surface gas exchange is greatly improved.

In another contemplated embodiment, the upward flow impeller is adapted for use in disposable bioreactors. The upward pumping impeller would preferably be located near or at the center of a disposable bioreactor, connecting to the driving motive force through a magnetic coupling. The plastic draft tube and vertical baffles can be pre-installed inside the disposable bag so they will be all sterilized prior to shipment to the end users. In the disposable embodiment of the bioreactor, the impeller is preferably constructed of inexpensive molded plastic that can be safely discarded after use, together with the bioreactor vessel or vessel liner.

Figure 3:
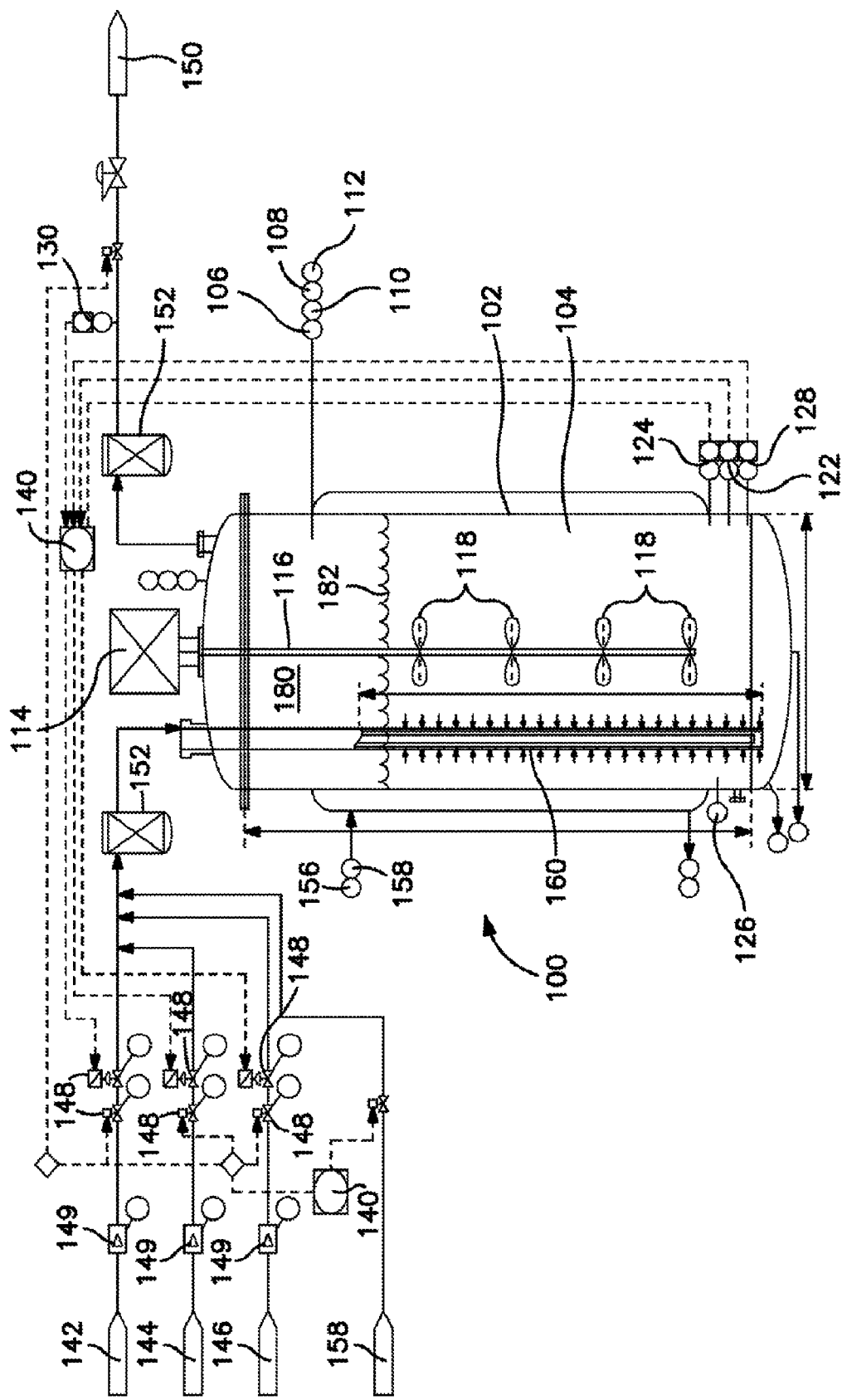
FIG. 3 is a schematic illustration of a bioreactor system employing the carbon dioxide stripping by means of the vertical gas-liquid riser and membrane isolator in accordance with another embodiment of the invention.

FIG. 3 illustrates another alternative embodiment of a bioreactor system adapted to control levels of dissolved carbon dioxide and consequently limit the level of osmolality in a mammalian cell culture process. The illustrated system 100 includes a bioreactor vessel 102 suitable for containing mammalian cell culture media 104, nutrients 106, additives 108, anti-foam agents 110 and inoculated mammalian cells 112. The system 100 includes a motor 114 which rotates a shaft 116 and drives propellers 118 to continuously mix the cell culture solution within the bioreactor vessel 102. Also included are a plurality of sensors and analyzers including a pH sensor 122, a $dCO_2$ sensor 124, a temperature indicator 126, a dissolved oxygen analyzer 128, and a vent gas analyzer 130. Such sensors and analyzers are coupled as inputs to the system controller 140 that controls or adjusts the gas supply of oxygen 142, nitrogen 144, and carbon dioxide 146 to the bioreactor vessel 102 through control of associated valves 148 and flow meters 149. The illustrated system 100 also includes an exhaust subsystem 150, a plurality of biological filters 152 and a means for sterilizing 154 the bioreactor vessel 102 with water 156 and steam 158, as needed.

In the embodiment of FIG. 3, the mammalian cells within the bioreactor vessel 102 are physically isolated from the turbulent mixing of the sparging gases. This is accomplished by sparging the air, nitrogen, oxygen, or other gases or combinations thereof into a vertical riser tube 160. The buoyancy force of the gas bubbles will force the liquid inside the tube 160 upward and eventually out of the tube 160. Oxygenation and carbon dioxide stripping occur between the gas bubbles and the rising liquid within the vertical riser tube 160. The riser tube 160 is enclosed in a porous membrane tube except for a top section of the riser tube extending into the headspace 180 above the surface 182 of the liquid in the bioreactor vessel 102. Since the top section of the riser tube 160 is not enclosed by the porous membrane, the rising liquid will exit the riser tube 160 and fall back into the bioreactor vessel 102.

The porous membrane preferably has pore sizes of about 5 micron or less which is sufficient to allow the cell culture media or solution to pass through but prevents the actual mammalian cells to pass. As the liquid leaves the riser tube, a differential pressure is created for driving additional cell culture media or solution through porous membrane into the riser tube. The membrane, however, prevents mammalian cells from entering the riser tube and thus shields the cells from the damage that occurs as a result of the gas-liquid mixing occurring therein.

Figure 4:
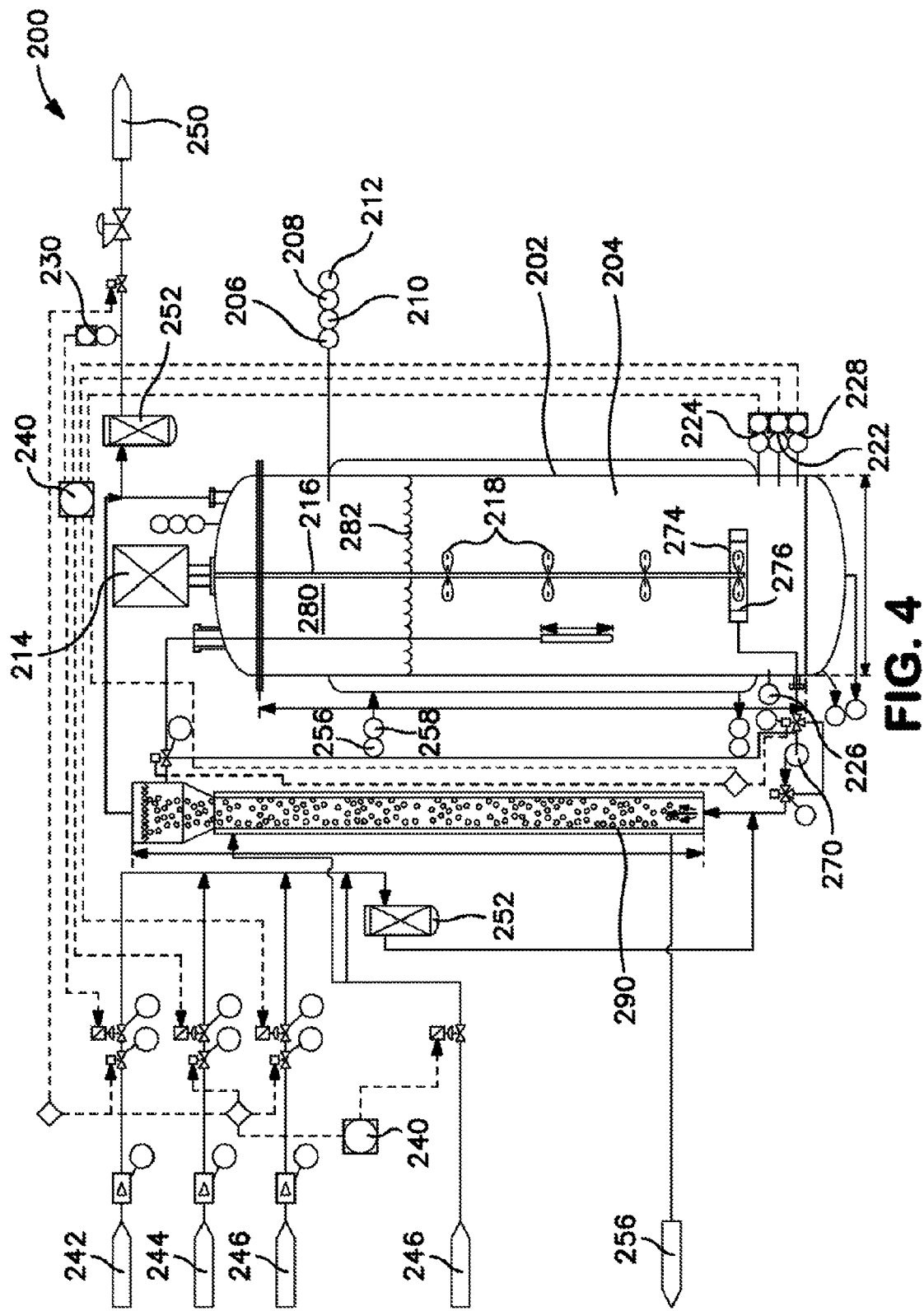
FIG. 4 is a schematic illustration of a bioreactor system employing a supersonic in-line stripper through which filtered media from the reaction vessel without the mammalian cells is diverted in accordance with another embodiment of the invention.

FIG. 4 shows yet another embodiment of a bioreactor system 200 adapted to control levels of dissolved carbon dioxide and consequently allow osmolality to be limited in a mammalian cell culture process. The illustrated system 200 includes a bioreactor vessel 202 suitable for containing mammalian cell culture media 204, nutrients 206, additives 208, anti-foam agents 210 and inoculated mammalian cells 212. The system 200 includes a motor 214 which rotates a shaft 216 and drives impellers or agitators 218 to continuously mix the cell culture solution within the bioreactor vessel 202. Also included are a plurality of sensors and analyzers including a pH sensor 222, a $dCO_2$ sensor 224, a temperature indicator 226, a dissolved oxygen analyzer 228, and a vent gas analyzer 230. Such sensors and analyzers are coupled as inputs to the system controller 240 that controls or adjusts the gas supply of oxygen 242, nitrogen 244, and carbon dioxide 246 to the bioreactor vessel 202 as well as the carbon dioxide stripping apparatus. The illustrated system 200 also includes an exhaust subsystem 250, a plurality of biological filters 252 and a means for sterilizing 254 the bioreactor vessel with water 256 and steam 258, as needed.

The carbon dioxide stripping apparatus is fluidically coupled to the bioreactor vessel 202 via a pump 270 and an intake apparatus 272. The intake apparatus 272 includes a metal housing 274 with a porous membrane 276 or metallic membrane facing the inside of the housing 274. This intake apparatus is preferably located at the same height as an impeller or agitator 218 within the bioreactor vessel 202.

The porous membrane 276 preferably has pore sizes of about 5 micron or less which is sufficient to allow the cell culture media 204 or solution to pass through but prevents the actual mammalian cells to pass. The alignment of the porous membrane 276 with the impeller or agitator 218 allows the rapid liquid flow radiating from the impeller to sweep away of any mammalian cells adhering or fouling to the surface of the porous membrane 276 and allows a continuous flow of cell culture media without the mammalian cells to be directed to the carbon dioxide stripping apparatus.

The filtered liquid without the mammalian cells flows through the pump 270 into the stripping apparatus 290. The stripping apparatus is preferably a supersonic in-line stripper or a bubbling column where rapid mixing, oxygenation and carbon dioxide removal can take place. Since no mammalian cells can enter the fine pores of the membrane unit, no cells will be damaged or killed by the turbulent two-phase flow in the supersonic in-line stripper. The stripping and oxygenating gases are disengaging from the top of the stripping apparatus 290 and exhausted 250 while the liquid is returned to the bioreactor vessel 202.

INDUSTRIAL APPLICABILITY

In addition to maintaining the desired nutrient and dissolved oxygen levels, conventional process control in commercial bioreactors currently focuses primarily upon regulating the pH level of the cell culture medium. Other important cell culture process parameters such as dissolved $CO_2$ concentration and osmolality remain essentially uncontrolled since the method of pH regulation—addition of base—acts to impede removal of dissolved $CO_2$ and causes osmolality to increase throughout the cell culture process. As a result, both dissolved $CO_2$ and osmolality can reach levels known to stress the cultured cells and negatively impact yield and productivity.

A further source of stress to the cultured cells is the gas delivered to the liquid in the bioreactor vessel as bubbles via a sparger. In some cases, small gas bubbles introduced via a sparger can directly damage sensitive cells and create excess foam, necessitating the addition of antifoam agents or additives that increases cost, interferes with the desired gas exchange mechanisms and may give rise to downstream purification issues.

All the above-identified stress factors are known to become more significant at commercial or larger bioreactor scales as the generally higher hydrostatic pressures lead to greater solubility of $CO_2$, greater volumes of sparged gases create more foam and larger agitators employed in commercial scale bioreactors tend to generate more cell damaging shear forces.

The combined effects of these stresses are lower cell growth rates, longer batch times, decreased productivity and yield, lower viability, increased cell lysis, more difficult process development and scale-up and degradation of protein products (by proteolytic enzymes released from bursting cells). Contents of the bursting cells also add to purification issues, particularly if antifoam has to be employed in the process. Finally, many of the stresses increase over time, leading to declining product quality, particularly in terms of the pattern, extent and homogeneity of glycosylation. In some cases, processes have to be terminated long before productivity ceases in order to make product of acceptable quality.

All the stresses listed in this section are mitigated or abolished by the bioreactor and bioreactor system modifications described herein. Reduction or elimination of the above-identified stresses has a significant impact on commercial cell culture manufacturing processes. Aside from increased yield and productivity, process development and scale-up is facilitated, product quality improved and purification simplified. In addition, the greater degree of process control attained leads to improved process robustness and reproducibility, in line with Quality By Design (QBD) principles.

From the foregoing, it should be appreciated that the present invention thus provides various methods and systems for controlling the dissolved carbon dioxide level during the mammalian cell culture process by stripping or removing excess dissolved carbon dioxide from the cell culture medium or solution. Numerous modifications, changes, and variations of the present methods and systems will be apparent to a person skilled in the art and it is to be understood that such modifications, changes, and variations are to be included within the purview of this application.

What is claimed is:

1. A bioreactor comprising:
   a bioreactor vessel containing a cell culture medium and defining a top liquid surface and a headspace above the top liquid surface;
   an impeller disposed in the bioreactor vessel to direct culture medium in the vessel in an upward direction toward the headspace to remove dissolved carbon dioxide from the cell culture medium into the headspace;
   a gas intake coupled to the bioreactor vessel proximate the headspace to receive a flow of sweep gas from one or more external sources of gas; and
   a gas exhaust coupled to the bioreactor vessel proximate the headspace to remove the sweep gas and carbon dioxide from the headspace of the bioreactor vessel to a vent.

2. The bioreactor of claim 1 wherein the impeller is a helical flow impeller.

3. The bioreactor of claim 1 further comprising a draft tube disposed around the impeller.

4. The bioreactor of claim 1 further comprising a vertical baffle system disposed proximate the impeller to orient the flow of the liquid proximate the impeller to a substantially vertical flow.

5. The bioreactor of claim 1 further comprising one or more sensors or analyzers selected from the group consisting of: carbon dioxide sensor, oxygen sensor; temperature sensor, pH sensor, and osmolality analyzer.

6. The bioreactor of claim 5 further comprising a controller to control: (i) the flow of sweep gas from the one or more external sources of gases to the headspace in the bioreactor vessel; (ii) the flow of sweep gas and removed carbon dioxide from the headspace in the bioreactor vessel to the vent; or (iii) the rotation of the impeller, in response to one or more sensors and analyzers.

7. The bioreactor of claim 6 wherein the sweep gas comprises oxygen or air.

8. The bioreactor of claim 7 wherein the controller further controls the composition of the sweep gas or the flow of the sweep gas in response to the dissolved oxygen level or dissolved carbon dioxide level in the culture medium.

9. The bioreactor of claim 2 wherein the helical impeller is disposed at a position within the bioreactor vessel that is below the top liquid surface in the bioreactor vessel during the cell culture process.

10. A bioreactor system for a cell culture process comprising:
    a bioreactor vessel containing a cell culture medium and defining a top liquid surface and a headspace above the top liquid surface;
    an upward flowing impeller disposed in the bioreactor vessel directing the culture medium in the bioreactor vessel in an upward direction toward the headspace;
    a gas intake coupled to the to the bioreactor vessel proximate the headspace to deliver a flow of sweep gas from one or more external sources of gas to the headspace of the bioreactor vessel; and
    a gas exhaust coupled to the bioreactor vessel proximate the headspace to remove a flow of the sweep gas and removed or striped carbon dioxide from the headspace of the bioreactor vessel to a vent;

wherein the upward flowing impeller continuously directs the culture medium in the bioreactor vessel in an upward direction toward the headspace to renew the cell culture medium at the top liquid surface and remove or strip dissolved carbon dioxide from the cell culture medium into the headspace.

11. The bioreactor system of claim 10 wherein the impeller is a helical flow impeller.

12. The bioreactor system of claim 10 further comprising a draft tube disposed around the impeller.

13. The bioreactor system of claim 10 further comprising a vertical baffle system disposed proximate the impeller to orient the flow of the liquid proximate the impeller to a substantially vertical flow.

14. The bioreactor of claim 10 further comprising one or more sensors or analyzers selected from the group consisting of: carbon dioxide sensor, oxygen sensor; temperature sensor, pH sensor, and osmolality analyzer.

15. The bioreactor of claim 14 further comprising a controller to control: (i) the flow of sweep gas from the one or more external sources of gases to the headspace in the bioreactor vessel; (ii) the flow of sweep gas and removed carbon dioxide from the headspace in the bioreactor vessel to the vent; or (iii) the rotation of the impeller, in response to one or more sensors and analyzers.

16. The bioreactor of claim 15 wherein the sweep gas comprises oxygen or air.

17. The bioreactor of claim 16 wherein the controller is further to adjust the composition of the sweep gas or the flow of the sweep gas in response to the dissolved oxygen level or dissolved carbon dioxide level in the culture medium.

18. The bioreactor of claim 11 wherein the helical impeller is disposed at a position within the bioreactor vessel below the top liquid surface in the bioreactor vessel during the cell culture process.

19. A bioreactor system of claim 15 wherein the osmolality of the cell culture medium is independently controlled.

20. An improvement to a method of culturing cells in a bioreactor vessel, the improvement comprising the steps of:
recirculating the cell culture medium within the bioreactor vessel in an upward direction toward a headspace in the bioreactor vessel to renew the cell culture medium at a top liquid surface and strip dissolved carbon dioxide from the cell culture medium into the headspace; and
directing a sweep gas through the headspace of the bioreactor vessel to remove the stripped carbon dioxide from the headspace of the bioreactor vessel to a vent.

21. The improvement of claim 20 wherein the step of recirculating the cell culture medium within the bioreactor vessel in an upward direction further comprises recirculating the cell culture medium in the bioreactor vessel using a helical flow impeller disposed in a draft tube.

22. The improvement of claim 20 wherein the step of recirculating the cell culture medium within the bioreactor vessel in an upward direction further comprises recirculating the cell culture medium in the bioreactor vessel using a helical flow impeller and a vertical baffle system disposed proximate the impeller to orient the flow of the liquid proximate the impeller to a substantially vertical flow.

23. The improvement of claim 20 further comprising the step of controlling the (i) the flow of sweep gas from the one or more external sources of gases to the headspace in the bioreactor vessel; (ii) the flow of sweep gas and removed carbon dioxide from the headspace in the bioreactor vessel to the vent; or (iii) the rotation of the impeller, in response to one or more sensors and analyzers selected from the group consisting of: carbon dioxide sensor, oxygen sensor; temperature sensor, pH sensor, and osmolality analyzer.

24. The improvement of claim 20 wherein the sweep gas comprises oxygen or air and further comprising the step of adjusting the composition of the sweep gas or the flow of the sweep gas in response to the dissolved oxygen level or dissolved carbon dioxide level in the cell culture medium.

* * * * *